US012720617B2

(12) United States Patent
Nakano et al.

(10) Patent No.: US 12,720,617 B2
(45) Date of Patent: Aug. 25, 2026

(54) WIRELESS COMMUNICATION SYSTEM AND WIRELESS COMMUNICATION DEVICE

(71) Applicant: Murata Manufacturing Co., Ltd., Nagaokakyo (JP)

(72) Inventors: Genta Nakano, Nagaokakyo (JP); Kota Tsubakizaka, Nagaokakyo (JP); Shuto Kimura, Nagaokakyo (JP); Takaya Sano, Nagaokakyo (JP); Hiroki Saitou, Nagaokakyo (JP); Koji Tanaka, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 545 days.

(21) Appl. No.: 18/336,862

(22) Filed: Jun. 16, 2023

(65) Prior Publication Data

US 2024/0008108 A1 Jan. 4, 2024

(30) Foreign Application Priority Data

Jun. 29, 2022 (JP) ................................ 2022-104830

(51) Int. Cl.

| | |
|---|---|
| ***H04W 76/10*** | (2018.01) |
| ***A61B 5/00*** | (2006.01) |
| ***A61B 5/01*** | (2006.01) |
| ***H04B 17/318*** | (2015.01) |

(52) U.S. Cl.

CPC ............... *H04W 76/10* (2018.02); *A61B 5/01* (2013.01); *A61B 5/6844* (2013.01); *H04B 17/318* (2015.01); *A61B 2562/0271* (2013.01)

(58) Field of Classification Search

CPC ....... H04W 76/10; H04B 17/318; A61B 5/01; A61B 5/6844; A61B 2562/0271

USPC .......................................................... 455/41.2

See application file for complete search history.

(56) References Cited

U.S. PATENT DOCUMENTS

| | | | | |
|---|---|---|---|---|
| 4,387,724 | A * | 6/1983 | Zartman ............. | A61D 17/002 600/549 |
| 10,753,803 | B2 * | 8/2020 | Ou Yang ............. | A61B 5/0008 |
| 10,884,160 | B2 * | 1/2021 | Shimuta ................... | A61B 5/01 |
| 11,197,641 | B2 * | 12/2021 | Tanaka ..................... | A61B 5/11 |
| 2003/0220582 | A1 * | 11/2003 | Zhu .................... | A61B 5/14539 600/549 |
| 2006/0173375 | A1 * | 8/2006 | Koch ....................... | G01K 7/42 374/E7.042 |

(Continued)

FOREIGN PATENT DOCUMENTS

| | | |
|---|---|---|
| JP | 2015-192282 A | 11/2015 |
| JP | 2020-134474 A | 8/2020 |
| JP | 2020198502 A | 12/2020 |

*Primary Examiner* — April G Gonzales

(74) *Attorney, Agent, or Firm* — ArentFox Schiff LLP

(57) ABSTRACT

A wireless communication system is provide that includes deep body temperature sensors that include a measured deep body temperature into an advertising packet that is then transmitted. A display unit displays a measurement result of a deep body temperature. When the wireless connection to the display unit is not established, each of the deep body temperature sensors includes a result of determination of whether it is stuck to a human body into an advertising packet and transmits the advertising packet. In an aspect, the display unit is wirelessly connected to a sensor stuck to a human body among the deep body temperature sensors.

20 Claims, 8 Drawing Sheets

(56) References Cited

U.S. PATENT DOCUMENTS

2008/0018480 A1* 1/2008 Sham .................. G01J 5/025 600/474
2008/0300819 A1* 12/2008 Koch .................. G01K 7/42 374/E7.042
2011/0051776 A1* 3/2011 Bieberich .............. G01K 13/20 600/549
2012/0063487 A1* 3/2012 Albrecht ................ G01J 5/049 374/128
2012/0114013 A1* 5/2012 Tsuchida ................ G01K 13/20 374/185
2012/0128024 A1* 5/2012 Tsuchida ................ G01K 13/20 374/E17.001
2015/0289217 A1* 10/2015 Ban .................... H04W 56/001 455/41.2
2017/0055896 A1* 3/2017 Al-Ali .................. A61B 5/01
2017/0326013 A1* 11/2017 Hyde .................. A61G 7/108
2018/0110415 A1* 4/2018 Sasahara .............. A61B 5/0008
2018/0132768 A1* 5/2018 Sasahara ............ A61B 5/14551
2019/0049317 A1* 2/2019 Tsuchimoto ........... G01K 7/427
2019/0350531 A1* 11/2019 Shimuta ............... A61B 5/6833
2019/0373377 A1* 12/2019 Larsen .................. A61B 5/1118
2020/0060553 A1* 2/2020 Tsuchimoto ........... G16H 50/20
2020/0271824 A1* 8/2020 Shimuta ............... A61B 5/6832
2020/0278260 A1* 9/2020 Shimuta ................... G01K 1/08
2020/0309608 A1* 10/2020 Shimuta ................... G01K 7/16
2020/0382877 A1* 12/2020 Larsen ................... H04R 25/02
2020/0383036 A1* 12/2020 Abe ........................ H04W 4/80
2021/0015079 A1* 1/2021 Gorski ................... A01K 29/00
2021/0038084 A1* 2/2021 Dion ........................ A61B 5/01
2021/0055168 A1* 2/2021 Niki ......................... G01K 7/16
2021/0076945 A1* 3/2021 Imamura .................. G01K 1/14
2021/0199514 A1* 7/2021 Shimuta ................... G01K 7/42
2021/0212606 A1* 7/2021 Tran ................... A61B 5/14532
2021/0259555 A1* 8/2021 Usui ........................ A61B 5/01
2021/0290184 A1* 9/2021 Ahmed ................ A61B 5/0008
2022/0042856 A1* 2/2022 Igawa ...................... G01K 7/16
2022/0079522 A1* 3/2022 Kaen .................... A61B 5/1135
2022/0167846 A1* 6/2022 Lee ........................ A61B 5/021
2022/0218256 A1* 7/2022 Thiagarajan ....... A61B 5/14532
2022/0346716 A1* 11/2022 Tsuchimoto ............. A61B 5/01

* cited by examiner

40
DISPLAY DEVICE
48
STORAGE DEVICE
44
COMMUNICATION DEVICE
46
PU
42
10 (1)
30
PU
32
STORAGE DEVICE
34
COMMUNICATION DEVICE
36
10 (2)
10 (3)
T2
26
T1
20
24
22
OUTSIDE AIR SIDE
SKIN SIDE

WIRELESS COMMUNICATION SYSTEM AND WIRELESS COMMUNICATION DEVICE

CROSS REFERENCE TO RELATED APPLICATIONS

This application claims priority to Japanese Patent Application No. 2022-104830, filed Jun. 29, 2022, the entire contents of which are hereby incorporated by reference in its entirety.

TECHNICAL FIELD

The present invention relates to a wireless communication system and a wireless communication device.

BACKGROUND

In an example, Japanese Unexamined Patent Application Publication No. 2020-198502 describes a wireless communication system using Bluetooth®. The wireless communication system described therein includes a communication apparatus and an information processing apparatus. The information processing apparatus includes a device for determining whether the information processing apparatus can be connected to the communication apparatus based on information about whether the communication apparatus is a stationary apparatus in addition to the intensity of radio waves of advertising information.

When the communication apparatus is in contact with a living body, the intensity of radio waves of advertising information is smaller in the information processing apparatus than that when the communication apparatus is not in contact with a living body. Accordingly, the information processing apparatus may fail to be appropriately connected to the communication apparatus when it is determined whether they can be connected in accordance with the intensity of radio waves.

SUMMARY OF THE INVENTION

In view of the foregoing, a wireless communication system is provided that includes a plurality of first wireless communication devices configured to transmit a state signal representing a state of contact with a living body and a second wireless communication device configured to perform connection processing and prioritizing processing. In this aspect, the connection processing is processing for establishing a wireless connection to one of the first wireless communication devices, and the prioritizing processing includes processing for performing, in response to an input of the state signal, the connection processing for the first wireless communication device that is in contact with the living body in preference to the first wireless communication device that is not in contact with the living body.

In the above-described configuration, the second wireless communication device can be configured to perform the connection processing when the first wireless communication device is in contact with the living body rather than when the first wireless communication device is not in contact with the living body. As a result, the appropriate wireless connection to the first wireless communication device can be established in, for example, the following cases. The first case is when the wireless connection to the first wireless communication device is intended when the first wireless communication device is in contact with the living body. The second case is when it is determined whether the wireless connection to the first wireless communication device is established based on a distance derived from the reception strength of a radio signal transmitted from the first wireless communication device.

DETAILED DESCRIPTION OF THE EMBODIMENTS

First Exemplary Embodiment

The first embodiment will be described below with reference to drawings.

System Configuration

Figure 1:
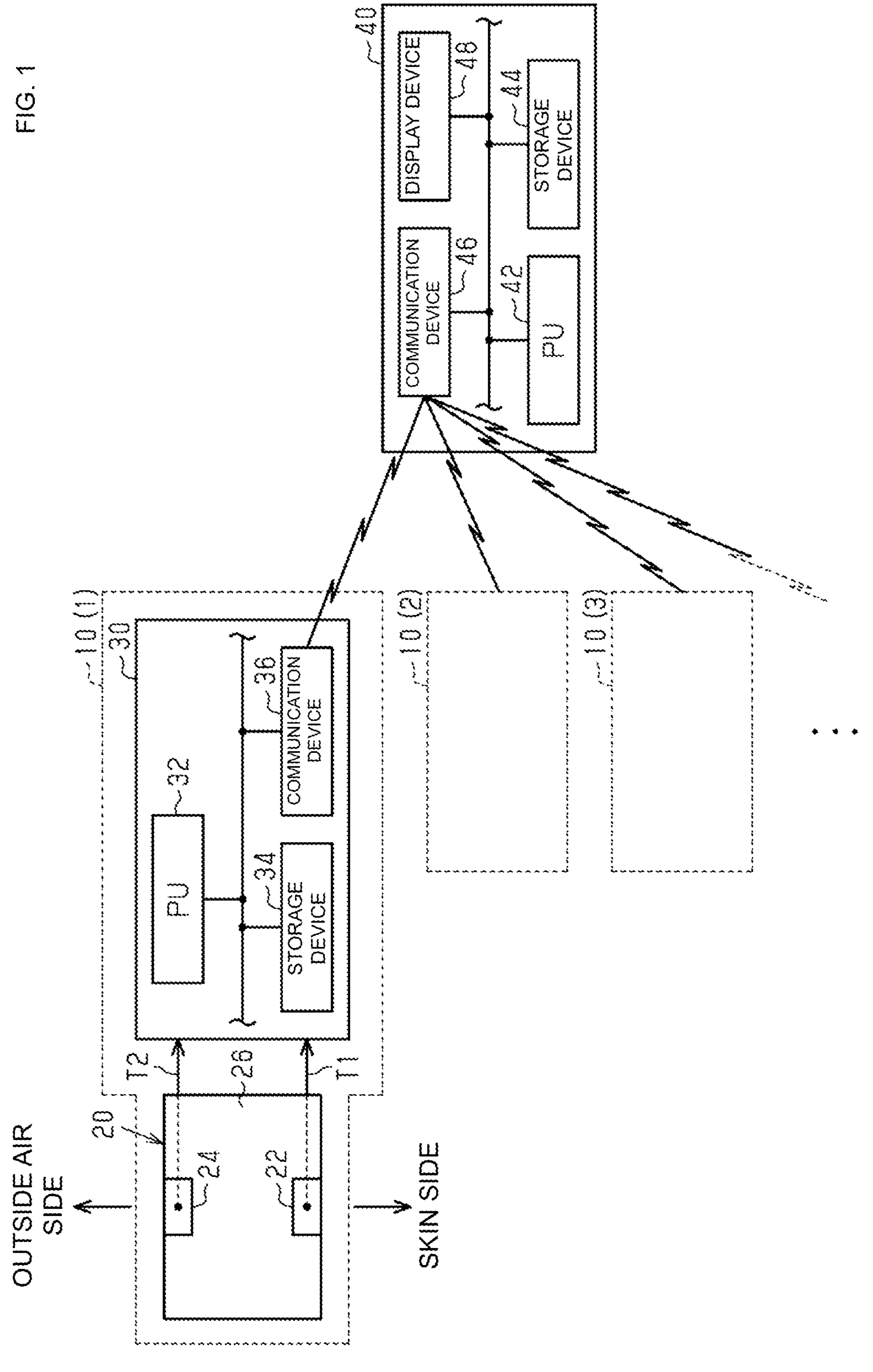
FIG. 1 is a diagram illustrating the configuration of a wireless communication system according to a first exemplary embodiment.

FIG. 1 is a diagram illustrating a wireless communication system according to an embodiment.

In the exemplary system, deep body temperature sensors 10(1), 10(2), etc., illustrated in FIG. 1 are sensors for detecting a person's deep body temperature. Figures in parentheses in numerals given to the deep body temperature sensors 10(1), 10(2), 10(3) . . . represent differences between individuals. It should be appreciated that while only three deep body temperature sensors are shown in the exemplary aspect, the system could use more or less such sensors in alternative aspects. Moreover, for purposes of this disclosure, the term "deep body temperature sensor" is used to collectively refer to the deep body temperature sensors 10(1), 10(2), 10(3) and the like.

In the exemplary aspect, the deep body temperature sensor includes a temperature detection unit 20 and a controller 30. The temperature detection unit 20 includes a first temperature sensor 22, a second temperature sensor 24, and a thermal resistor 26. The first temperature sensor 22 and the second temperature sensor 24 may be, for example, thermistors. The thermal resistor 26 is sandwiched between the first temperature sensor 22 and the second temperature sensor 24. The first temperature sensor 22 is disposed more closely to a human body than the second temperature sensor 24. Accordingly, the second temperature sensor 24 faces the human body across the thermal resistor 26. Specifically, the deep body temperature sensor is fixed at, for example, a predetermined position of the human body.

The controller 30 is configured to measure a person's deep body temperature on the basis of a first temperature T1 detected by the first temperature sensor 22 and a second temperature T2 detected ty the second temperature sensor 24. The controller 30 includes a PU 32, a storage device 34, and a communication device 36. The PU 32 is a software processor, such as a CPU, a GPU, or a TPU, in the exemplary aspects. The storage device 34 may be a storage medium, such as an electrically rewritable nonvolatile memory or a disc medium. The PU 32 performs a processing for measuring a deep body temperature by executing a program stored in the storage device 34. The communication device 36 is a device for wirelessly communicating with a display unit 40. In the present embodiment, the Bluetooth® standard is employed as a communication method used for communication between the deep body temperature sensor 10 and the display unit 40. Specifically, the Bluetooth low energy (BLE) standard is employed.

The display unit 40 is configured to display a measurement result of a deep body temperature transmitted from the deep body temperature sensor 10. The display unit 40 includes a PU 42, a storage device 44, a communication device 46, and a display device 48. The PU 42 is a software processor, such as a CPU, a GPU, or a TPU. The storage device 44 may be a storage medium, such as an electrically rewritable nonvolatile memory or a disc medium. The PU 42 performs a processing for displaying a measurement result by executing a program stored in the storage device 44.

Processing for Establishing Wireless Connection

The display unit 40 selectively establishes wireless connection to one of the deep body temperature sensors 10(1), 10(2), . . . . The establishment of wireless connection means that the display unit 40 selectively performs bidirectional communication with one of the deep body temperature sensors 10(1), 10(2), . . . . In a period in which one of the deep body temperature sensors 10(1), 10(2), . . . is wirelessly connected to the display unit 40, the bidirectional communication between another one of the deep body temperature sensors 10(1), 10(2), . . . and the display unit 40 is not performed.

Control for selectively establishing wireless connection is indented to set a connection target as follows. That is, the control is indented to set one of the deep body temperature sensors 10(1), 10(2), . . . which actually measures a person's deep body temperature as a connection target. When multiple ones of the deep body temperature sensors 10(1), 10(2), . . . actually measure a person's deep body temperatures, the control is intended to set the sensor closest to the display unit 40 as a connection target. This will be described below with reference to FIGS. 2 to 5.

Figure 2:
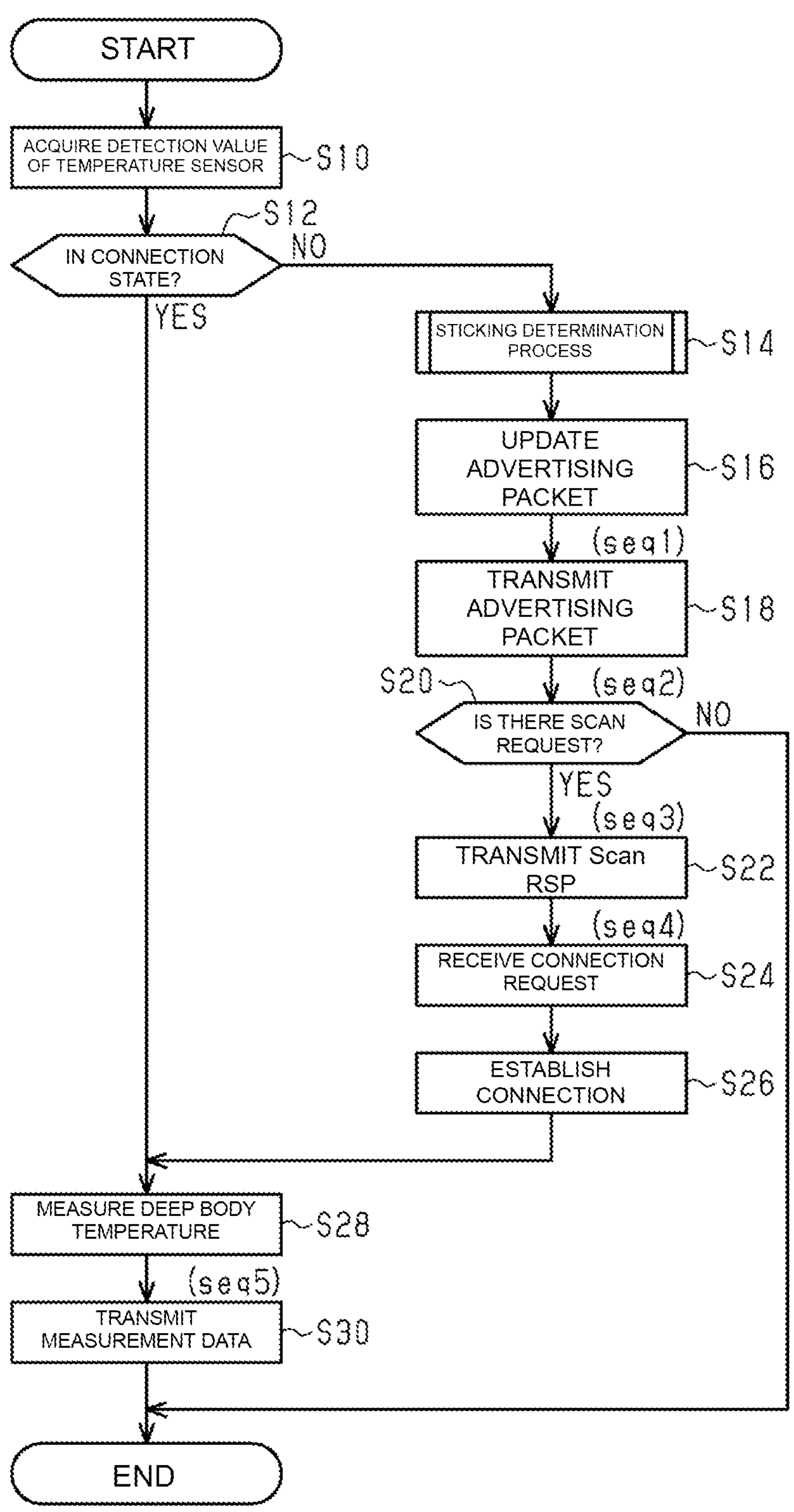
FIG. 2 is a flowchart illustrating a process performed by a deep body temperature sensor according to the first exemplary embodiment.
Figure 3:
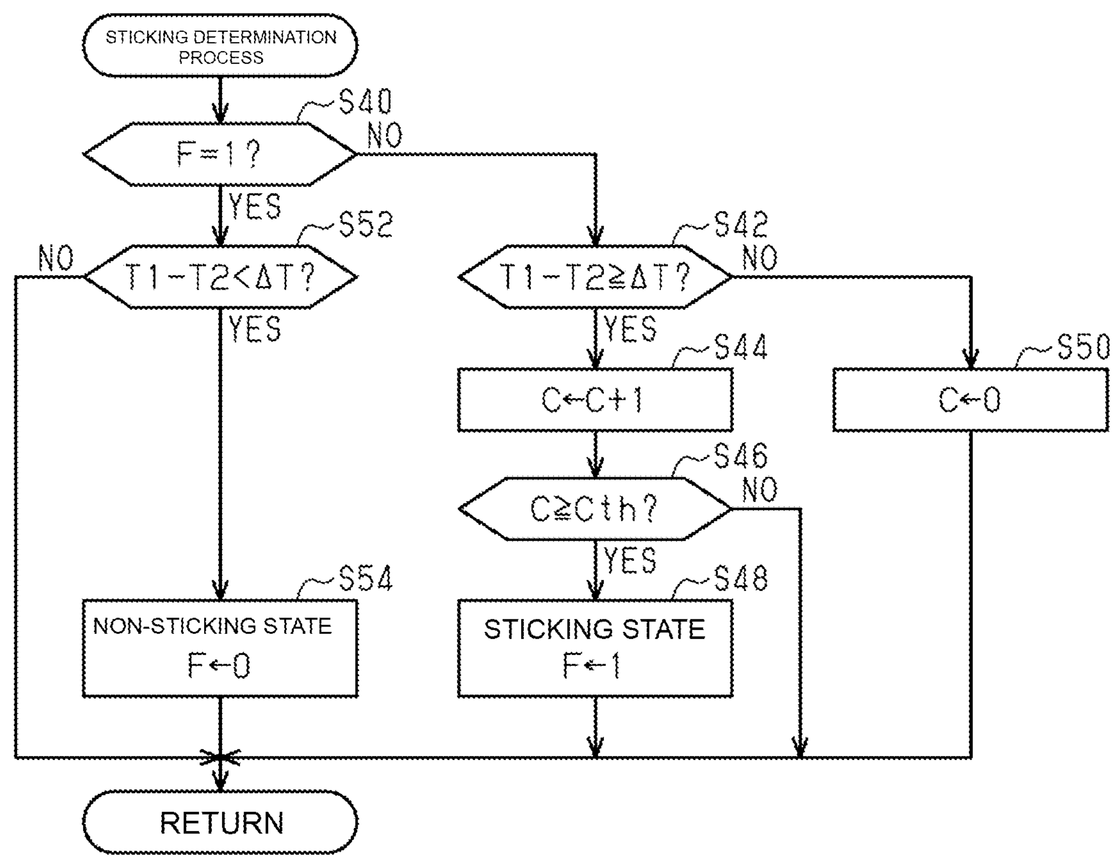
FIG. 3 is a flowchart illustrating a detailed process of a part of the process performed by a deep body temperature sensor according to the first exemplary embodiment.

FIG. 2 illustrates a process that the deep body temperature sensor 10 performs as a peripheral. The PU 32 repeatedly executes a program stored in the storage device 34, for example, on predetermined cycles, so that the process illustrated in FIG. 2 is performed. FIG. 3 illustrates a detailed process of a part of the process illustrated in FIG. 2. In the following, step numbers of the respective pieces of processing are expressed by numbers following the initial letter "S."

Figure 4:
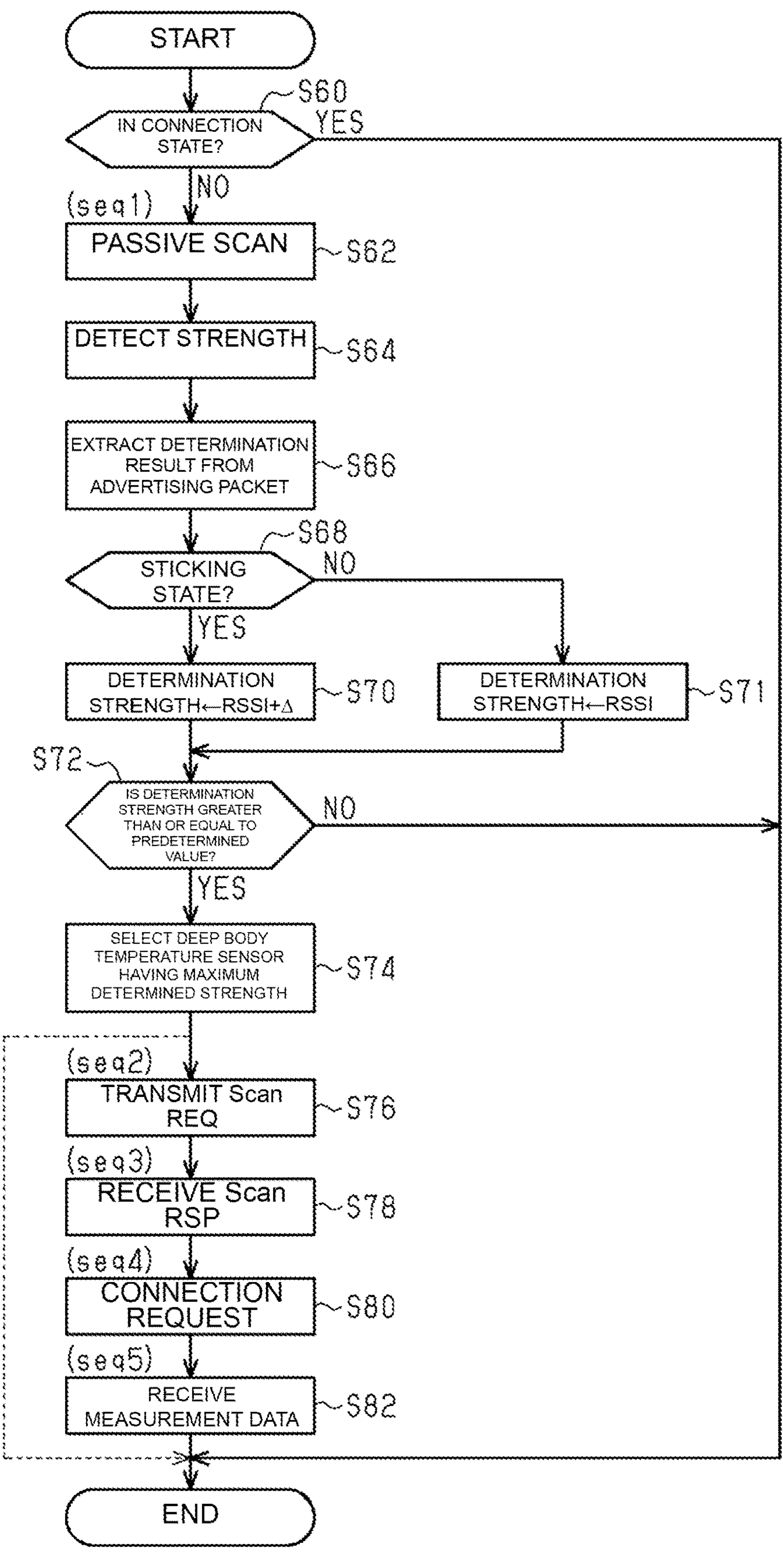
FIG. 4 is a flowchart illustrating a process performed by a display unit according to the first exemplary embodiment.

FIG. 4 illustrates a process that the display unit 40 performs as a central unit. The PU 42 repeatedly executes a program stored in the storage device 44, for example, on predetermined cycles, so that the process illustrated in FIG. 4 is performed.

Figure 5:
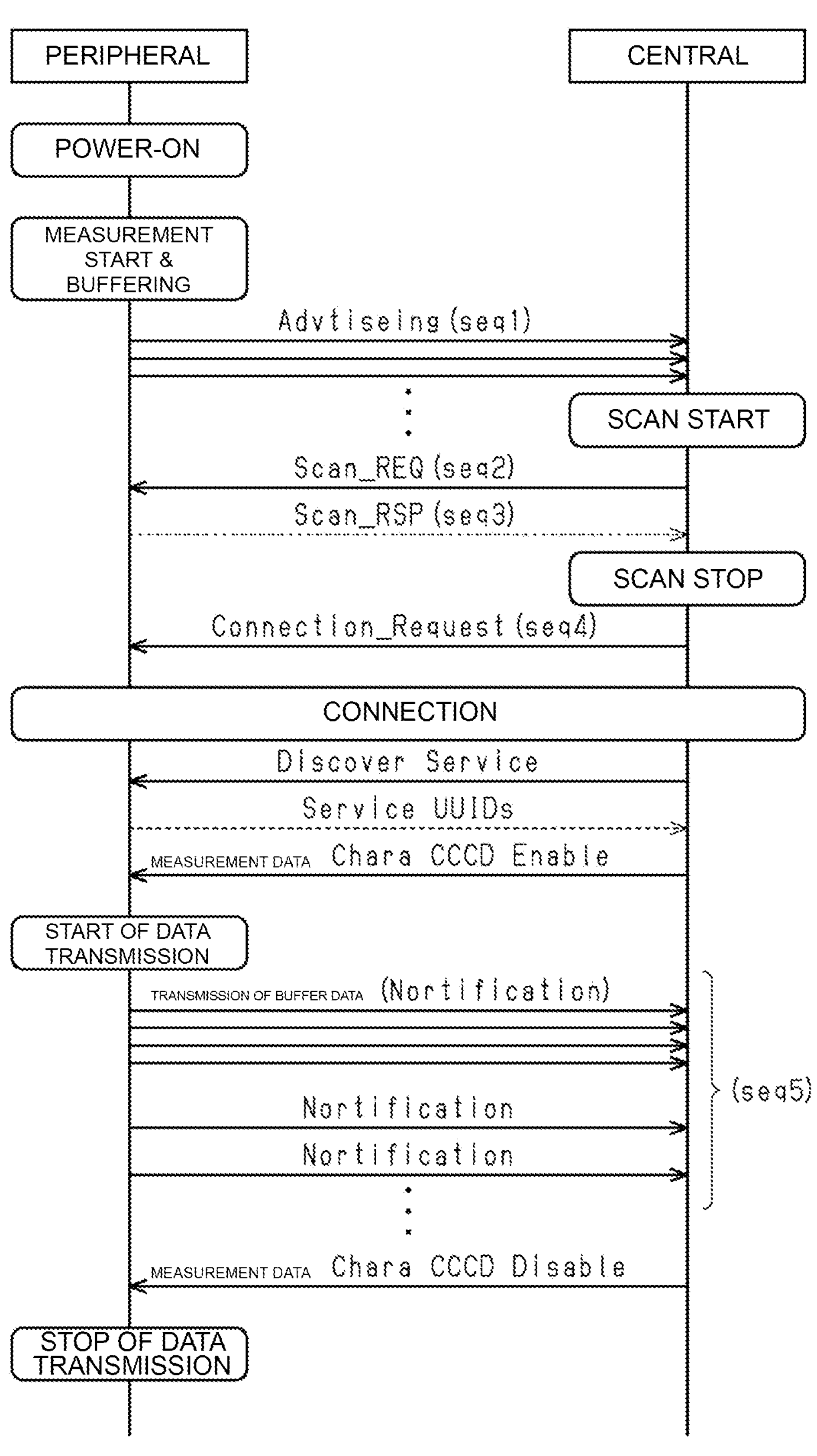
FIG. 5 is a time chart of an exemplary communication sequence according to the first exemplary embodiment.

FIG. 5 exemplifies a communication sequence executed by the processes illustrated in FIGS. 2 to 4. Referring to FIGS. 2 to 4, the symbols of "seq1" to "seq5" are added to respective pieces of processing corresponding to the sequence illustrated in FIG. 5. The processes illustrated in FIGS. 2 to 4 will be described below in chronological order up to the establishment of wireless connection.

In the process illustrated in FIG. 2, the PU 32 in the deep body temperature sensor 10 acquires the first temperature T1 detected by the first temperature sensor 22 and the second temperature T2 detected by the second temperature sensor 24 (S10). Subsequently, the PU 32 determines whether the wireless connection to the display unit 40 is established, that is, it is in the state of connection to the display unit 40 (S12). When determining that wireless connection is not established (S12: NO), the PU 32 performs a process of determining whether the deep body temperature sensor 10 is stuck to a human body (S14).

FIG. 3 illustrates a detailed process of the processing of S14.

In the process illustrated in FIG. 3, the PU 32 determines whether a status flag F is "1" (S40). The status flag F of "1" indicates that the deep body temperature sensor 10 is stuck to a human body. On the other hand, the status flag F of "0" indicates that the deep body temperature sensor 10 is not stuck to a human body. When determining that the status flag F is "0" (S40: NO), the PU 32 determines whether a value obtained by subtracting the second temperature T2 from the first temperature T1 is greater than or equal to a threshold value ΔT (S42). When determining that the value is greater than or equal to the threshold value ΔT (S42: YES), the PU 32 increments a counter C by only "1" (S44). Then, the counter C measures the duration of time a result of the subtraction is greater than or equal to the threshold value ΔT. Subsequently, the PU 32 determines whether the counter C is greater than or equal to a threshold value Cth (S46). This processing is performed for the determination of whether the deep body temperature sensor 10 is stuck to a human body. That is, when the deep body temperature sensor 10 is stuck to a human body, the first temperature T1 is obtained closer to the human body than the second temperature T2. In particular, the second temperature T2 is the temperature of the thermal resistor 26 to which heat is transferred from a human body. The heat from the human body decreases with increasing distance from the first temperature sensor 22 to the second temperature sensor 24. Accordingly, the second temperature T2 is lower than the first temperature T1. The threshold value Cth is set to a value for suppression of a determination error due to noise.

When determining that the counter C is greater than or equal to the threshold value Cth (S46: YES), the PU 32 substitutes "1" into the status flag F as a result of the determination that the deep body temperature sensor 10 is stuck to a human body (S48). On the other hand, when determining that the counter C is less than the threshold value ΔT (S42: NO), the PU 32 initializes the counter C (S50).

When determining that the status flag F is "1" (S40: YES), the PU 32 determines whether the value obtained by subtracting the second temperature T2 from the first temperature T1 is less than the threshold value ΔT (S52). When determining that a result of the subtraction is less than the threshold value ΔT (S52: YES), the PU 32 substitutes "0" into the status flag F as a result of the determination that the deep body temperature sensor 10 is not stuck to a human body (S54).

The PU 32 ends the processing of S14 illustrated in FIG. 2 when completing the processing of S48, S50, or S54 or when making a negative determination in S46 or S52. Referring back to FIG. 2, the PU 32 updates an advertising packet on the basis of a result of the determination in S14

(S16). That is, the advertising packet includes data regarding a result of the determination in S14. The processing of S16 includes processing for updating data regarding a result of the determination in S14 which is included in the advertising packet to the latest data.

Subsequently, the PU 32 transmits the advertising packet by operating the communication device 36 (S18). Data transmitted in S18 includes data specifying the deep body temperature sensor 10. That is, for example, when the PU 32 in the deep body temperature sensor 10(1) performs the processing of S18, data specifying the deep body temperature sensor 10(1) is included. This processing is performed to notify the display unit 40, which is a central device, that the deep body temperature sensor 10(1) can be wirelessly connected to the display unit 40.

On the other hand, the PU 42 in the display unit 40 is configured to determine whether the display unit 40 is connected to one of the multiple deep body temperature sensors 10(1), 10(2), . . . as illustrated in FIG. 4 (S60). When determining that there is no wireless connection to any of the multiple deep body temperature sensors 10(1), 10(2), . . . (S60: NO), the PU 42 performs a passive scan to receive an advertising signal from the deep body temperature sensor 10 around it (S62). As a result, the advertising packet transmitted in S18 is received. Referring to FIG. 5, "seq1" is added to the sequence regarding the pieces of processing of S18 and S62.

Subsequently, the PU 42 detects a reception strength RSSI that is the strength of a received advertising signal (S64). This processing may be performed by including data for the detection of the reception strength RSSI into an advertising packet. Subsequently, the PU 42 extracts a determination result from the advertising packet (S66). The PU 42 determines whether the extracted determination result indicates that the deep body temperature sensor is stuck to a human body (S68). When determining that the extracted determination result indicates that the deep body temperature sensor is stuck to a human body (S68: YES), the PU 42 increases the value of the reception strength RSSI for compensation and substitutes the value into a determination strength (S70).

The processing of step S70 is aimed for the following exemplary aspects (a) and (b).

(a) When the deep body temperature sensor 10 is stuck to a human body, the reception strength RSSI decreases as compared with the case where the deep body temperature sensor 10 is not stuck to a human body. This decrease is compensated for. That is, a human body contains a predetermined amount of moisture. The frequency band of radio waves used in wireless communication in the present embodiment is easily absorbed by moisture. This frequency band is, for example, the "2.4 GHz band". Accordingly, the reception strength RSSI more easily decreases in the case where the deep body temperature sensor 10 is stuck to a human body as compared with the case where the deep body temperature sensor 10 is not stuck to a human body even if the distance between the deep body temperature sensor 10 and the display unit 40 does not change in both cases.

(b) Preferably, the deep body temperature sensor 10 stuck to a human body is connected wirelessly to the display unit 40. As described above, a target of connection to the display unit 40 is the deep body temperature sensor 10 stuck to a human body in the present embodiment. Accordingly, in order to increase the possibility that the deep body temperature sensor 10 stuck to a human body will be selected in S74 to be described below, a determination strength is increased for the level of the reception strength RSSI.

On the other hand, when determining that the determination result indicates that the deep body temperature sensor is not stuck to a human body (S68: NO), the PU 42 substitutes the reception strength RSSI into a determination strength (S71).

The PU 42 determines whether the determination strength is greater than or equal to a predetermined value when completing the processing of S70 or S71 (S72). This processing is performed to exclude the deep body temperature sensor 10 that is too far away from the display unit 40 from connection targets. Among the multiple deep body temperature sensors 10(1), 10(2), . . . , the sensors from which respective advertising signals have been able to be received in S62 are all subjected to the process from S64 to S72.

When determining that the determination strength of at least one of the multiple deep body temperature sensors 10(1), 10(2), . . . is greater than or equal to the predetermined value (S72: YES), the PU 42 selects the deep body temperature sensor 10 having the highest strength (S74). When there is no deep body temperature sensor 10, the determination strength of which is greater than or equal to the predetermined value, the process illustrated in FIG. 4 ends as represented by a broken line in FIG. 4.

In the following, it is assumed that the deep body temperature sensor 10 having the highest determination strength is the deep body temperature sensor 10(1) for the convenience of explanation. Subsequently, the PU 42 goes to an active scan mode by transmitting a scan request to the selected deep body temperature sensor 10(1) by operating the communication device 46 (S76).

On the other hand, the PU 32 in the deep body temperature sensor 10(1) determines whether there is a scan request as illustrated in FIG. 2 (S20). Referring to FIG. 5, "seq2" is added to the sequence corresponding to the pieces of processing of S76 and S20. When determining that there is a scan request (S20: YES), the PU 32 responds to the scan request (S22). That is, the PU 32 transmits a "scan response" by operating the communication device 36.

On the other hand, the PU 42 in the display unit 40 receives the "scan response" as illustrated in FIG. 4 (S78). Referring to FIG. 5, "seq3" is added to the sequence corresponding to the pieces of processing of S22 and S78.

Referring back to FIG. 4, the PU 42 transmits a connection request to the deep body temperature sensor 10(1) by operating the communication device 46 (S80). On the other hand, the PU 32 in the deep body temperature sensor 10(1) receives the connection request as illustrated in FIG. 2 (S24). Referring to FIG. 5, "seq4" is added to the sequence corresponding to the pieces of processing of S80 and S24.

Referring back to FIG. 2, the PU 32 establishes the wireless connection to the display unit 40 (S26).

When completing the processing of S26 or when making a positive determination in S12, the PU 32 measures a deep body temperature (S28). The PU 32 transmits measurement data of a deep body temperature to the display unit 40 by operating the communication device 36 (S30). When completing the processing of S30 or when making a negative determination in S20, the PU 32 ends the process illustrated in FIG. 2.

On the other hand, the PU 42 in the display unit 40 receives the measurement data (S82 in FIG. 4). Referring to FIG. 5, "seq5" is added to the sequence corresponding to the pieces of processing of S30 and S82. When completing the processing of S82 or when making a negative determination in S60 or S72, the PU 42 ends the process illustrated in FIG. 4.

After S80 and S26, the PU 32 and the PU 42 perform some pieces of processing illustrated in FIG. 5 before the transmission and reception of measurement data.

Operation and Effect of Present Embodiment

When the deep body temperature sensor 10 is powered on, the PU 32 in the deep body temperature sensor 10 is configured to determine whether the deep body temperature sensor 10 is stuck to a human body. The PU 32 includes a determination result into an advertising packet and transmits an advertising signal to notify the display unit 40 of the presence of the deep body temperature sensor 10.

The PU 42 in the display unit 40 is in an advertising signal reception state when it is not wirelessly connected to any of the multiple deep body temperature sensors 10(1), 10(2), . . . . The PU 42 calculates the reception strength RSSI of a received advertising signal and then extracts a result of determination of whether the deep body temperature sensor 10 is stuck to a human body from data included in the advertising signal. The PU 42 increases the reception strength RSSI of the advertising signal received from the deep body temperature sensor 10 stuck to a human body for compensation and sets the reception strength RSSI as a determination strength. The PU 42 establishes the wireless connection to the deep body temperature sensor 10 that has the highest determination strength of the deep body temperature sensors 10 from which the PU 42 has received respective advertising signals.

It is desired that the deep body temperature sensor 10 stuck to a human body be wirelessly connected to the display unit 40 for display of the measurement result of a deep body temperature on the display unit 40. In general, a human body is largely composed of water. The strength of radio waves in a frequency band used in the communication between the deep body temperature sensor 10 and the display unit 40 easily decreases because of water. Accordingly, the reception strength RSSI more easily decreases in the case where the deep body temperature sensor 10 is stuck to a human body as compared with the case where the deep body temperature sensor 10 is not stuck to a human body even if the distance between the deep body temperature sensor 10 and the display unit 40 does not change in both cases. Therefore, there is concern that the deep body temperature sensor 10 desired to be wirelessly connected to the display unit 40 will not be determined as a connection target on the basis of only the reception strength RSSI.

By using a determination strength obtained by increasing the reception strength RSSI for compensation as described above, the decrease in the reception strength RSSI when the deep body temperature sensor 10 is stuck to a human body has a smaller influence on the determination of a connection target.

The above setting of (b) means as follows. That is, even if the deep body temperature sensor 10 stuck to a human body is farther away from the display unit 40 than the deep body temperature sensor 10 that is not stuck to a human body by a predetermined distance, the determination strength of the deep body temperature sensor 10 stuck to a human body is higher than that of the deep body temperature sensor 10 that is not stuck to a human body. Accordingly, the deep body temperature sensor 10 stuck to a human body can be preferentially set as a target of connection to the display unit 40.

According to the present embodiment described above, operations and effects to be described below can be further obtained.

(1-1) In an exemplary aspect, the PU 42 in the display unit 40 sets the deep body temperature sensor 10 as a candidate for a connection target on condition that a determination strength based on a signal transmitted from the deep body temperature sensor 10 is greater than or equal to a predetermined value. Accordingly, the deep body temperature sensor 10 that is too far away from the display unit 40 can be prevented from being set as a candidate for a connection target. When the deep body temperature sensor 10 is stuck to a human body, the PU 42 obtains a determination strength by increasing the reception strength RSSI for compensation. In the condition that the deep body temperature sensor 10 from which the reception strength RSSI greater than or equal to a predetermined strength is obtained is set as a candidate for a connection target, the predetermined strength of the reception strength RSSI is therefore smaller in the case where the deep body temperature sensor 10 is stuck to a human body as compared with case where the deep body temperature sensor 10 is not stuck to a human body. Accordingly, even if the reception strength RSSI decreases for the distance to the display unit because of the sticking of the deep body temperature sensor 10 to a human body, the deep body temperature sensor is likely to be set as a candidate for a connection target.

(1-2) The deep body temperature sensor 10 transmits to the display unit 40 a signal in which data regarding a result of determination whether the deep body temperature sensor 10 is stuck to a human body is included in an advertising packet. The display unit 40 can therefore quickly determine whether the deep body temperature sensor is stuck to a human body.

(1-3) The PU 32 in the deep body temperature sensor determines whether the deep body temperature sensor 10 is stuck to a human body based on the first temperature T1 and the second temperature T2 input thereto. The second temperature sensor 24 for outputting the second temperature T2 faces a human body across the thermal resistor 26. Accordingly, the difference between the second temperature T2 and the first temperature T1 is likely to be made when the deep body temperature sensor 10 is stuck to a human body. On the other hand, both the first temperature T1 and the second temperature T2 are likely to be close to an outside air temperature when the deep body temperature sensor 10 is not stuck to a human body. It can therefore be accurately determined whether the deep body temperature sensor 10 is stuck to a human body by using the first temperature T1 and the second temperature T2.

Second Exemplary Embodiment

The second embodiment will be described below with reference to the drawing focusing on the difference between the first embodiment and the second embodiment.

In the exemplary aspect, the PU 42 determines a target of connection to the display unit 40 based on a determination strength having a positive correlation with the reception strength RSSI in the above first embodiment. In the present embodiment, the deep body temperature sensor 10 that is not stuck to a human body is excluded from candidates for a connection target.

Figure 6:
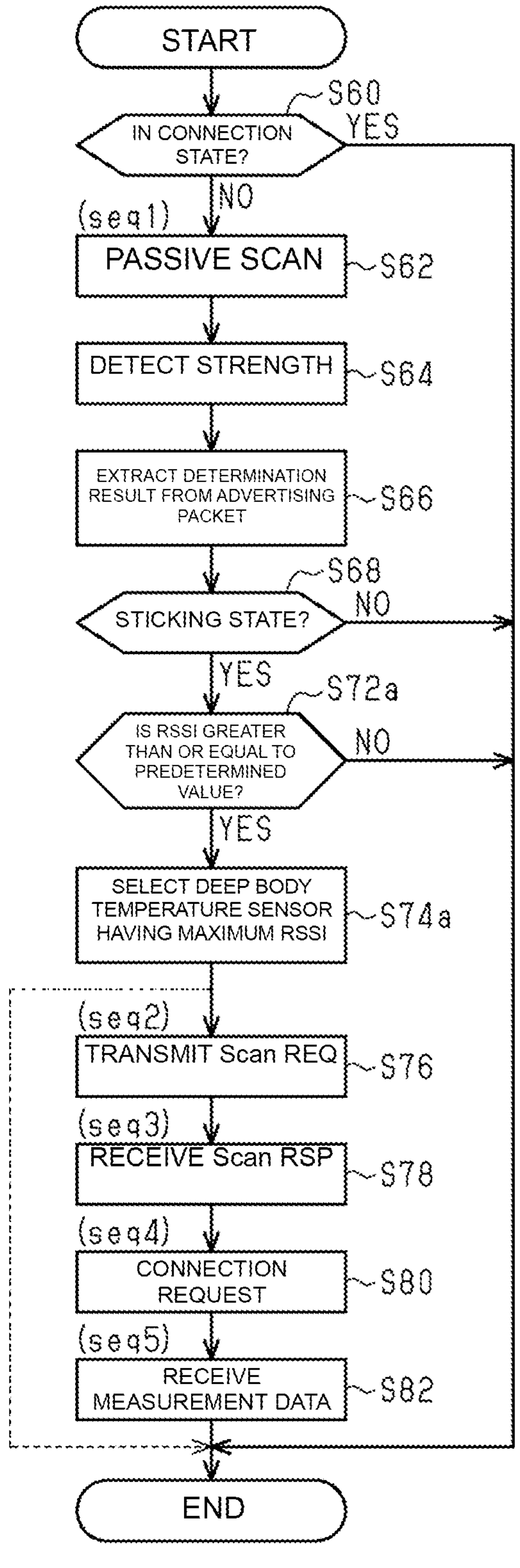
FIG. 6 is a flowchart illustrating a process performed by a display unit according to a second exemplary embodiment.

FIG. 6 illustrates a process performed by the PU 42 in the display unit 40. Referring to FIG. 6, processing corresponding to the processing illustrated in FIG. 4 is given the same step number for convenience and the description thereof will be omitted.

When the PU 42 determines that the deep body temperature sensor 10 is not stuck to a human body in the process illustrated in FIG. 6 (S68: NO), the PU 42 ends the process illustrated in FIG. 6 to exclude the deep body temperature sensor 10 from candidates for a connection target.

On the other hand, when determining that the deep body temperature sensor 10 is stuck to a human body (S68: YES), the PU 42 determines whether the reception strength RSSI is greater than or equal to a predetermined value (S72*a*). When determining that the reception strength RSSI is greater than or equal to the predetermined value (S72*a*: YES), the PU 42 selects the deep body temperature sensor 10 having the highest reception strength RSSI (S74*a*). When there is no deep body temperature sensor 10 having the reception strength RSSI greater than or equal to the predetermined value, the PU 42 ends the process illustrated in FIG. 6 as represented by a broken line in FIG. 6.

On the other hand, after selecting the deep body temperature sensor 10 having the highest reception strength RSSI, the PU 42 performs the process from S76. When determining that the reception strength RSSI is less than the predetermined value (S72*a*: NO), the PU 42 ends the process illustrated in FIG. 6.

According to the present embodiment described above, the following operational effect can be obtained in addition to (1-2) and (1-3) in the first embodiment described above.

(2-1) The PU 42 in the display unit 40 excludes the deep body temperature sensor 10 that is not stuck to a human body from candidates for a connection target. As a result, a sensor to be connected to the display unit 40 can be limited to a sensor that is measuring a deep body temperature among the deep body temperature sensors 10(1), 10(2), 10(3) and the like.

Third Exemplary Embodiment

The third embodiment will be described below with reference to the drawing focusing on the difference between the first embodiment and the third embodiment.

In the first embodiment described above, the PU 32 in the deep body temperature sensor 10 performs the process illustrated in FIG. 3. On the other hand, the PU 42 in the display unit 40 performs the process illustrated in FIG. 3 in the present embodiment.

Figure 7:
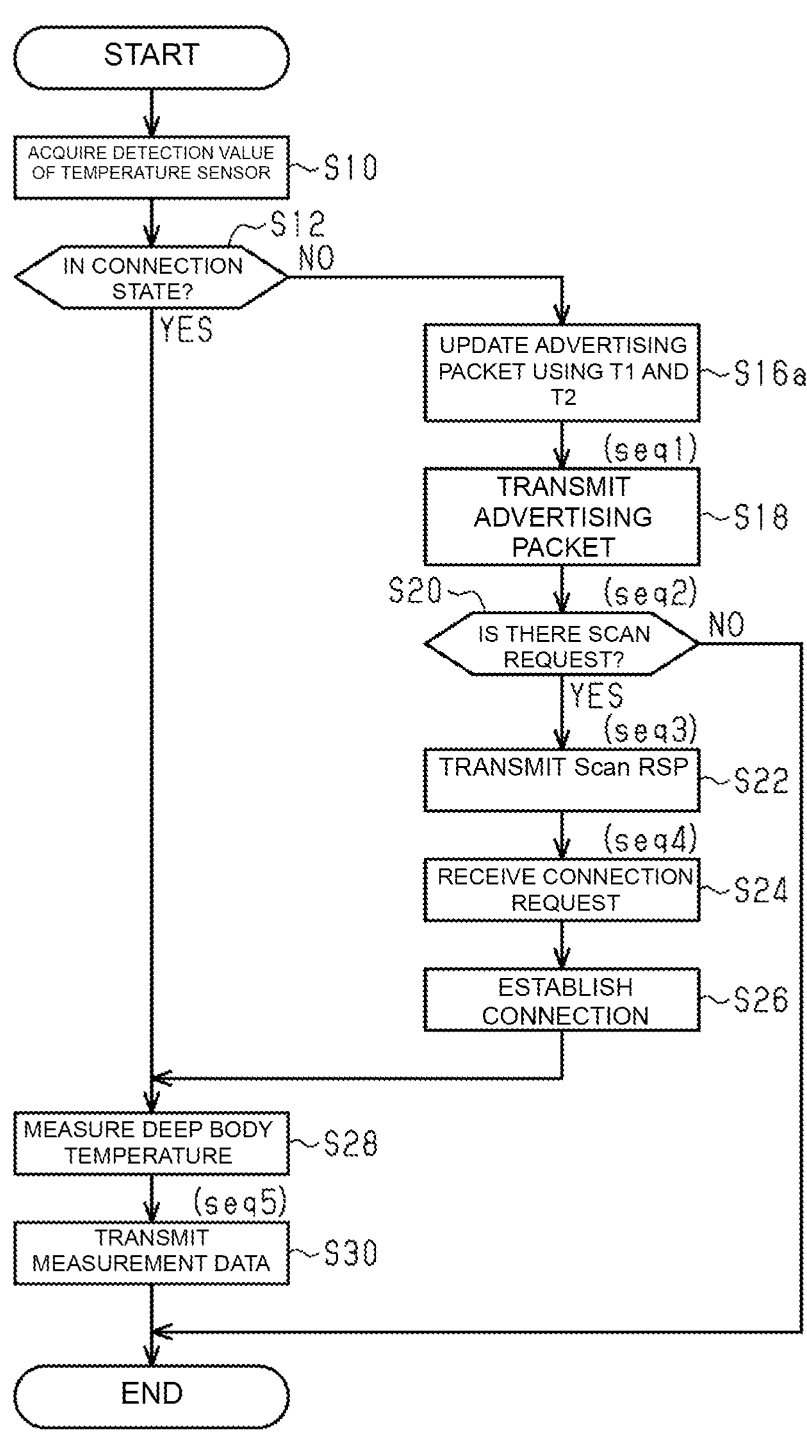
FIG. 7 is a flowchart illustrating a process performed by a deep body temperature sensor according to the second exemplary embodiment.

FIG. 7 illustrates the process performed by the PU 32 in the deep body temperature sensor 10 according to the present embodiment. The PU 32 repeatedly executes a program stored in the storage device 34, for example, on predetermined cycles, so that the process illustrated in FIG. 7 is performed. Referring to FIG. 7, processing corresponding to the processing illustrated in FIG. 2 is given the same step number and the description thereof will be omitted.

In the process illustrated in FIG. 7, the PU 32 updates the first temperature T1 and the second temperature T2 included in an advertising packet to a value obtained by the processing of S10 when making a negative determination in S12 (S16*a*). That is, the first temperature T1 and the second temperature T2 are included in an advertising packet in addition to a determination result obtained by the process illustrated in FIG. 3 in the present embodiment.

After completing the processing of S16*a*, the PU 32 performs the processing of S18.

Figure 8:
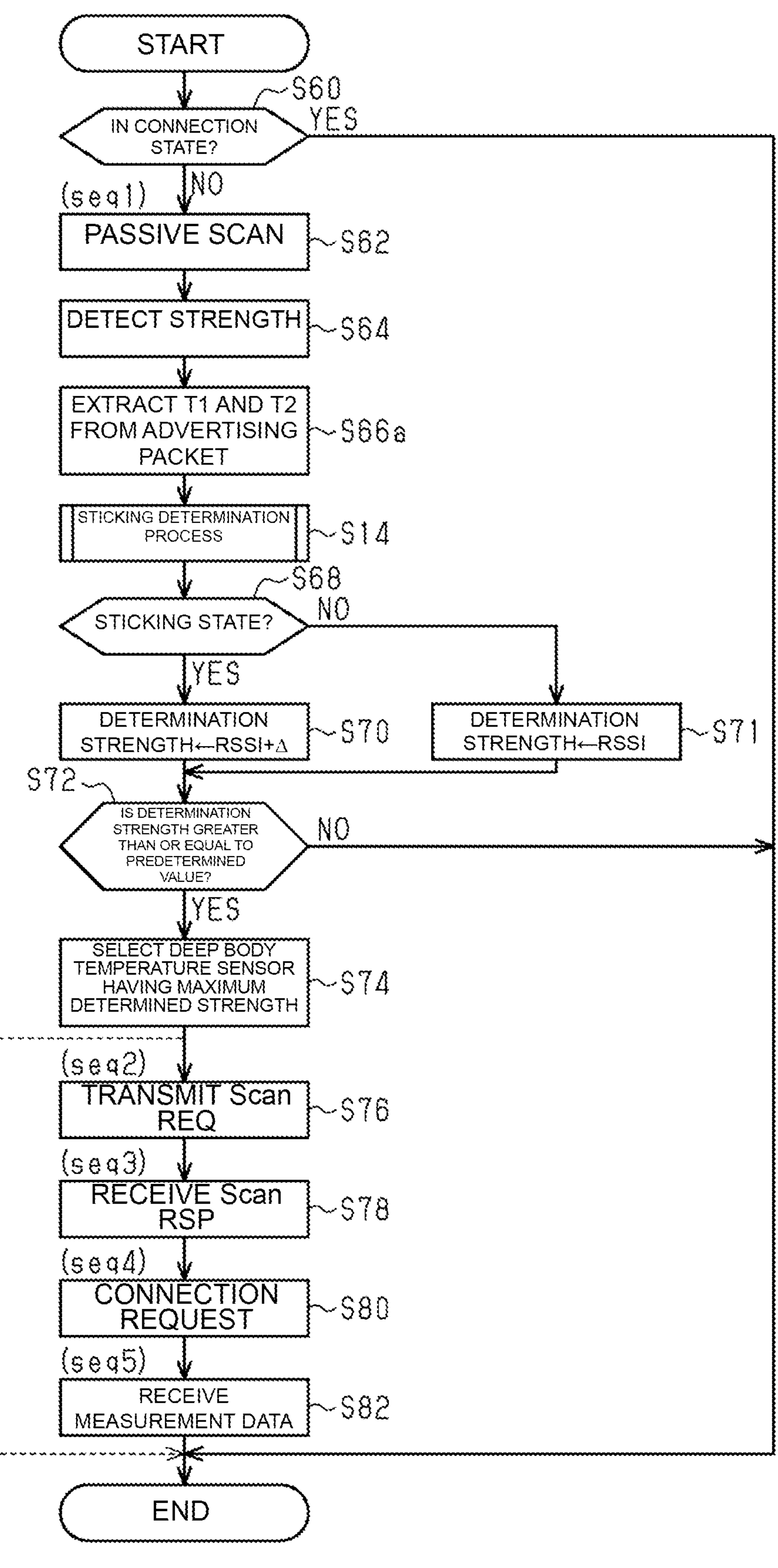
FIG. 8 is a flowchart illustrating a process performed by a display unit according to the second exemplary embodiment.

FIG. 8 illustrates the process performed by the PU 42 in the display unit 40 according to the present embodiment. The PU 42 repeatedly executes a program stored in the storage device 44, for example, on predetermined cycles, so that the process illustrated in FIG. 8 is performed. Referring to FIG. 8, processing corresponding to the processing illustrated in FIG. 4 is given the same step number and the description thereof will be omitted.

In the process illustrated in FIG. 8, the PU 42 performs processing for extracting the first temperature T1 and the second temperature T2 from an advertising packet instead of the processing of S66 illustrated in FIG. 4 (S66*a*). After completing the processing of S14 in FIG. 2, the PU 42 performs the processing of S68.

According to the present embodiment described above, the following operational effect can be obtained in addition to (1-1) and (1-3) in the first embodiment described above.

(3-1) The PU 42 in the display unit 40 determines whether the deep body temperature sensor 10 is stuck to a human body. As compared with the case where the PU 32 in the deep body temperature sensor 10 performs this determination, the computational burden on the deep body temperature sensor 10 can be reduced.

Correspondence

The correspondence between the items in the above-described embodiments and the items to be described below in "Appendix" is as follows. In the following, the correspondence is given for each of the numbers in the examples described in "Appendix". [1] A first wireless communication device corresponds to the deep body temperature sensor 10. A second wireless communication device corresponds to the display unit 40. Connection processing corresponds to the processing of S80. Prioritizing processing corresponds to the process from S68 to S70 in FIGS. 4 and 8 and non-performance of the process from S72*a* when a negative determination is made in S68 in FIG. 6. For purposes of this disclosure, the phrase "comprising a plurality of first wireless communication devices" corresponds to the presence of the multiple deep body temperature sensors 10 that can be candidates for a target of connection to the display unit 40 in FIG. 1. [2] Strength detection processing corresponds to processing of S64. Selection processing corresponds to the processing of S74. A reception strength corresponds to the reception strength RSSI detected by the processing of S64. The reception strength and the determination strength are the same when the processing of S70 is not performed while the determination strength is higher than the reception strength when the processing of S70 is performed. Accordingly, the level of the determination strength relative to the reception strength is higher when the processing of S70 is performed. [3] The sentence corresponds to the non-performance of the process from S72*a* when a negative determination is made in S68 in FIG. 6. [4 and 5] Strength detection processing corresponds to the processing of S64. Strength determination processing corresponds to the processing of S72 in FIGS. 4 and 8 and the processing of S72*a* in FIG. 6. The predetermined strength in FIGS. 4 and 8 corresponds to the predetermined value in S72 in the non-sticking state. The predetermined strength in FIGS. 4 and 8 corresponds to a value obtained by subtracting the amount of increase for compensation in S70 from the predetermined value in S72 in the sticking state. [6] Contact determination processing corresponds to the process illustrated in FIG. 3. A sensor corresponds to the temperature detection unit 20. [7] The sentence corresponds to the processes illustrated in FIGS. 7 and 8. A state signal corresponds to a signal representing an advertising packet including the first temperature T1 and the second temperature T2. A sensor corresponds to the temperature detection unit 20. [8] A first temperature sensor, a second temperature sensor, and a thermal resistor correspond to the first temperature sensor 22, the second temperature sensor 24, and the thermal resistor 26, respectively.

[9] A wireless communication device corresponds to the deep body temperature sensor 10. A wireless communication device corresponds to the display unit 40. Reception processing corresponds to the processing of S62. Prioritizing processing corresponds to the process from S68 to S70 in FIGS. 4 and 8 and non-performance of the process from S72*a* when a negative determination is made in S68 in FIG. 6.

Additional Exemplary Embodiments

It is noted that the present embodiments may be modified as follows. The present embodiments and the exemplary modifications to be described below may be combined with each other within the bounds of not causing a technical contradiction.

State Signal

A state signal with which the display unit 40 can know the presence or absence of contact of a living body without determining the presence or absence of contact of the living body is not limited to a signal in which data representing a determination result in S14 is included in an advertising packet. For example, when the deep body temperature sensor 10 measures a deep body temperature only when the deep body temperature sensor 10 is in contact with a living body, the following signal may be set as a state signal. That is, a signal in which data representing each deep body temperature or data indicating that a deep body temperature cannot be measured may be set as a state signal.

In S18 in FIG. 7, data representing the first temperature T1 and the second temperature T2 is included in an advertising packet. For example, data representing the difference between the first temperature T1 and the second temperature T2 may be included in an advertising packet.

Prioritizing Processing

Processing for changing the level of a determination strength relative to a reception strength on the basis of the presence or absence of contact is not limited to the process from S68 to S71. For example, a value obtained by reducing the reception strength RSSI for compensation may be substituted into a determination strength in S71, and the reception strength RSSI may be substituted into a determination strength in S70. Alternatively, a value obtained by reducing the reception strength RSSI for compensation may be substituted into a determination strength in S71, and a value obtained by increasing the reception strength RSSI for compensation into a determination strength in S70.

Processing for changing the level of a determination strength relative to a reception strength on the basis of the presence or absence of contact is not limited to processing for changing the relative level as described in the above embodiments. For example, instead of the processing of S70, processing may be performed for increasing the reception strength RSSI for compensation to set the same determination strength in the case of the same distance regardless of the presence or absence of contact with a living body.

Strength Determination Processing

Instead of the processing of S72, processing for comparing the reception strength RSSI and a threshold value may be employed. In this case, a threshold value in a contact state is set to be smaller than that in a non-contact state. The threshold value represents a predetermined strength.

Processing for determining whether the reception strength RSSI is higher than or equal to a predetermined strength does not necessarily have to be provided.

Contact Determination Processing

In the case where a sensor for detecting the state of a living body is a sensor for measuring a heart rate as will be described below in “Sensor”, it may be determined that the present state is a contact state when a heart rate in the possible range of a heart rate of a living body is measured. In the case where a sensor for detecting the state of a living body is a pulse oximeter as will be described below in “Sensor”, it may be determined that the present state is a contact state when an oxygen concentration in the possible range of an oxygen concentration of a living body is measured. In the case where a sensor for detecting the state of a living body is a sensor for detecting the two or more states of a living body as will be described below in “Sensor”, the presence or absence of contact of a living body may be determined on the basis of measurement results of two or more states of a living body.

Living Body

A living body is not limited to a human body, and may be, for example, the body of an experimental mouse.

Deep Body Temperature Sensor

A deep body temperature sensor is not limited to a sensor including the temperature detection unit 20 illustrated in FIG. 1.

Sensor

A sensor for detecting the state of a living body is not limited to a deep body temperature sensor, and may be, for example, a sensor for measuring a heart rate or a pulse oximeter in alternative aspects. A sensor for detecting the state of a living body does not necessarily have to be a sensor for detecting a single kind of state of a living body, and may be, for example, a sensor for detecting two more states of a living body, such as a deep body temperature and a heart rate.

First Wireless Communication Device

A first wireless communication device does not necessarily have to include a sensor, and may include, for example, a storage device storing the personal information of a user. A wireless connection to the first wireless communication device in contact with a living body can be preferentially established for, for example, the acquisition of the personal information of the user.

It is also noted that the first wireless communication device is not limited to one that executes software processing. For example, the first wireless communication device may include a dedicated hardware circuit, such as an ASIC, that performs at least a part of the processes performed in the above embodiments. That is, the first wireless communication device may include one of the following processing circuits (a) to (c): (a) a processing circuit including a processing device that executes all of the above-described processes in accordance with programs and a program storage device that stores these programs; (b) a processing circuit including a processing device that executes a part of the above-described processes in accordance with programs, a program storage device, and a dedicated hardware circuit that executes the remaining part of the processes; and (c) a processing circuit including a dedicated hardware circuit that executes all of the above-described processes. Here, a plurality of software execution devices including a processing device and a program storage device or a plurality of dedicated hardware circuits may be provided.

Second Wireless Communication Device

The second wireless communication device is not limited to one that executes software processing. For example, in alternative aspects, the second wireless communication device may include a dedicated hardware circuit, such as an ASIC, that performs at least a part of the processes performed in the above embodiments. That is, the second wireless communication device may include one of the following processing circuits (a) to (c): (a) a processing circuit including a processing device that executes all of the above-described processes in accordance with programs and a program storage device that stores these programs; (b) a processing circuit including a processing device that executes a part of the above-described processes in accordance with programs, a program storage device, and a dedicated hardware circuit that executes the remaining part of the processes; and (c) a processing circuit including a dedicated hardware circuit that executes all of the above-described processes. Here, a plurality of software execution devices including a processing device and a program storage device or a plurality of dedicated hardware circuits may be provided.

Wireless Communication System

A wireless communication system does not necessarily have to include the multiple deep body temperature sensors 10. Even in the case where only the single deep body temperature sensor 10 is provided, the process from S68 to S71 can be performed when the PU 42 performs the processing of S72. In this case, the PU 42 determines whether to perform connection processing on the basis of whether the determination strength is greater than or equal to a predetermined value. That is, when the determination strength is less than the predetermined value, the PU 42 does not perform connection processing. When the determination strength is greater than or equal to the predetermined value, the PU 42 performs connection processing. By the pieces of processing of S70 and S72, the determination strength in the state of contact with a living body is higher than that in the state of non-contact with a living body.

Additional Aspect

A communication method is not limited to BLE.

Appendix

Technical ideas that are derived from the above embodiments and the above exemplary modifications will be described below.

In an exemplary aspect, a wireless communication system is provided that includes a plurality of first wireless communication devices configured to transmit a state signal representing a state of contact with a living body; and a second wireless communication device configured to perform connection processing and prioritizing processing. Moreover, the connection processing is configured for establishing a wireless connection to one of the first wireless communication devices, the prioritizing processing includes processing for performing, in response to an input of the state signal, the connection processing for the first wireless communication device that is in contact with the living body in preference to the first wireless communication device that is not in contact with the living body.

In the wireless communication system according to 1, the second wireless communication device is configured to perform strength detection processing and selection processing. In this aspect, the strength detection processing is processing for detecting a reception strength of a signal transmitted from the first wireless communication device. Moreover, the selection processing is processing for selecting a start of communication with the first wireless communication device having a determination strength that is highest of determination strengths of the plurality of first wireless communication devices, the determination strength being a variable having a positive correlation with the reception strength. The prioritizing processing includes processing for making a level of the determination strength relative to the reception strength of a signal transmitted from the first wireless communication device that is in contact with the living body higher than a level of the determination strength relative to the reception strength of a signal transmitted from the first wireless communication device that is not in contact with the living body.

In the wireless communication system according to 1, the prioritizing processing includes processing for not establishing a wireless connection when the first wireless communication device is not in contact with the living body.

In the wireless communication system according to any one of 1 to 3, the second wireless communication device is configured to perform strength detection processing and strength determination processing, the strength detection processing being processing for detecting a reception strength of a signal transmitted from the first wireless communication device, the strength determination processing being processing for determining whether the reception strength is higher than or equal to a predetermined strength. The connection processing is processing for establishing a wireless connection to the first wireless communication device on condition that the reception strength is higher than or equal to the predetermined strength. The prioritizing processing includes processing for making the predetermined strength when there is contact with the living body lower than the predetermined strength when there is no contact with the living body.

In another exemplary aspect, a wireless communication system is provided that includes a first wireless communication device configured to transmit a state signal representing a state of contact with a living body; and a second wireless communication device configured to perform strength detection processing, strength determination processing, and prioritizing processing. In this aspect, the strength detection processing is processing for detecting a reception strength of a signal transmitted from the first wireless communication device, the strength determination processing is processing for determining whether the reception strength is higher than or equal to a predetermined strength, the connection processing is processing for establishing a wireless connection to the first wireless communication device on condition that the reception strength is higher than or equal to the predetermined strength, the prioritizing processing includes processing for making the predetermined strength when there is contact with the living body lower than the predetermined strength when there is no contact with the living body.

In the wireless communication system according to any one of 1 to 5, the first wireless communication device is configured to perform contact determination processing for determining whether there is contact with the living body in response to an input of a detection value of a sensor configured to detect a state of the living body. The state signal is a signal representing a determination result of the contact determination processing.

In the wireless communication system according to any one of 1 to 5, the first wireless communication device is configured to perform state signal transmission processing for transmitting the state signal. The second wireless communication device is configured to perform contact determination processing for determining whether there is contact with the living body in response to an input of the state signal. The state signal transmission processing is processing for transmitting the state signal in response to an input of a detection value of a sensor configured to detect a state of the living body.

In the wireless communication system according to 6 or 7, the sensor includes a first temperature sensor, a second temperature sensor, and a thermal resistor. The first temperature sensor is disposed closer to the living body than the second temperature sensor. The second temperature sensor faces the first temperature sensor across the thermal resistor.

A wireless communication device is provided that is configured to transmit a state signal to an external wireless communication device, the state signal being a signal representing presence or absence of a state of contact with a living body.

Moreover, a wireless communication device is provided that is configured to perform reception processing, connection processing, and prioritizing processing, the reception processing being processing for receiving a transmitted signal from an external wireless communication device in a state in which a wireless connection to the external wireless communication device is not established, the transmitted signal including a state signal representing presence or absence of a state of contact between the external wireless communication device and a living body, the connection processing being processing for establishing a wireless connection to the external wireless communication device, the prioritizing processing including processing for prioritizing, in response to an input of the state signal, the connection processing when the external wireless communication device is in contact with the living body rather than when the external wireless communication device is not in contact with the living body.

In general, it is noted that the exemplary embodiments described above are intended to facilitate the understanding of the present invention, and are not intended to limit the interpretation of the present invention. The present invention may be modified and/or improved without departing from the spirit and scope thereof, and equivalents thereof are also included in the present invention. That is, exemplary embodiments obtained by those skilled in the art applying design change as appropriate on the embodiments are also included in the scope of the present invention as long as the obtained embodiments have the features of the present invention. For example, each of the elements included in each of the embodiments, and arrangement, materials, conditions, shapes, sizes, and the like thereof are not limited to those exemplified above, and may be modified as appropriate. It is to be understood that the exemplary embodiments are merely illustrative, partial substitutions or combinations of the configurations described in the different embodiments are possible to be made, and configurations obtained by such substitutions or combinations are also included in the scope of the present invention as long as they have the features of the present invention.

What is claimed:

1. A wireless communication system comprising:

a plurality of first wireless communication devices configured to transmit a state signal that represents a state of physical contact with a living body, wherein the state signal includes an advertising pack comprising a determination result that indicates whether one first wireless communication device of the plurality of first wireless communication devices is in physical contact with the living body; and a second wireless communication device configured to:

perform a connection processing that establishes a wireless connection to the one first wireless communication device of the plurality of first wireless communication devices, and perform prioritizing processing that includes performing, in response to an input of the state signal, the connection processing for the one first wireless communication device that is in physical contact with the living body in preference to a first wireless communication device of the plurality of first wireless communication devices that is not in physical contact with the living body.

2. The wireless communication system according to claim 1, wherein the second wireless communication device is configured to perform strength detection processing for detecting a reception strength of a signal transmitted from the one first wireless communication device.

3. The wireless communication system according to claim 2, wherein the second wireless communication device is configured to perform selection processing for selecting a start of communication with the one first wireless communication device having a determination strength that is highest of determination strengths of the plurality of first wireless communication devices, with the determination strength being a variable having a positive correlation with the reception strength.

4. The wireless communication system according to claim 3, wherein the second wireless communication device is further configured to perform the prioritizing processing by making a level of the determination strength relative to the reception strength of a signal transmitted from the one first wireless communication device that is in physical contact with the living body higher than a level of the determination strength relative to the reception strength of a signal transmitted from the first wireless communication device that is not in physical contact with the living body.

5. The wireless communication system according to claim 1, wherein the second wireless communication device is further configured to perform the prioritizing processing by not establishing a wireless connection when the one first wireless communication device is not in physical contact with the living body.

6. The wireless communication system according to claim 1, wherein the second wireless communication device is further configured to:

perform strength detection processing by detecting a reception strength of a signal transmitted from the one first wireless communication device, and perform strength determination processing by determining whether the reception strength is higher than or equal to a predetermined strength.

7. The wireless communication system according to claim 6, wherein the second wireless communication device is further configured to perform connection processing by establishing a wireless connection to the one first wireless communication device when the reception strength is higher than or equal to the predetermined strength.

8. The wireless communication system according to claim 7, wherein the second wireless communication device is further configured to perform the prioritizing processing by making the predetermined strength when there is physical contact with the living body lower than the predetermined strength when there is no physical contact with the living body.

9. The wireless communication system according to claim 1, wherein the first wireless communication device is configured to perform contact determination processing for determining whether there is physical contact with the living body in response to an input of a detection value of a sensor configured to detect a state of the living body.

10. The wireless communication system according to claim 9, wherein the state signal represents the determination result of the contact determination processing.

11. The wireless communication system according to claim 1, wherein the first wireless communication device is further configured to perform state signal transmission processing for transmitting the state signal.

12. The wireless communication system according to claim 11, wherein the second wireless communication device is further configured to perform contact determination processing for determining whether there is physical contact with the living body in response to an input of the state signal.

13. The wireless communication system according to claim 12, wherein the state signal transmission processing comprises transmitting the state signal in response to an input of a detection value of a sensor configured to detect a state of the living body.

14. The wireless communication system according to claim 13, wherein the sensor includes a first temperature sensor, a second temperature sensor, and a thermal resistor, wherein the first temperature sensor is disposed closer to the living body than the second temperature sensor, and wherein the second temperature sensor faces the first temperature sensor across the thermal resistor.

15. A wireless communication system comprising:

a first wireless communication device configured to transmit a state signal that represents a state of physical contact with a living body, the state signal including an advertising pack comprising a determination result that indicates whether the first wireless communication device is in physical contact with the living body; and a second wireless communication device configured to:

perform strength detection processing by detecting a reception strength of a signal transmitted from the first wireless communication device, perform strength determination processing by determining whether the reception strength is higher than or equal to a predetermined strength, perform a connection processing by establishing a wireless connection to the first wireless communication device when the reception strength is higher than or equal to the predetermined strength, and perform prioritizing processing by setting the predetermined strength when there is physical contact with the living body lower than the predetermined strength when there is no physical contact with the living body.

16. The wireless communication system according to claim 15, wherein the first wireless communication device is configured to perform contact determination processing for determining whether there is physical contact with the living body in response to an input of a detection value of a sensor configured to detect a state of the living body.

17. The wireless communication system according to claim 16, wherein the state signal represents the determination result of the contact determination processing.

18. The wireless communication system according to claim 15, wherein the first wireless communication device is further configured to perform state signal transmission processing for transmitting the state signal wherein the second wireless communication device is further configured to perform contact determination processing for determining whether there is physical contact with the living body in response to an input of the state signal, and wherein the state signal transmission processing comprises transmitting the state signal in response to an input of a detection value of a sensor configured to detect a state of the living body.

19. The wireless communication system according to claim 18, wherein the sensor includes a first temperature sensor, a second temperature sensor, and a thermal resistor, wherein the first temperature sensor is disposed closer to the living body than the second temperature sensor, and wherein the second temperature sensor faces the first temperature sensor across the thermal resistor.

20. A wireless communication device comprising:

a memory; and a processor configured to execute instructions on the memory that, when executed, cause the processor to:

perform reception processing for receiving a transmitted signal from an external wireless communication device in a state in which a wireless connection to the external wireless communication device is not established, with the transmitted signal including a state signal representing presence or absence of a state of physical contact between the external wireless communication device and a living body, wherein the state signal includes an advertising pack comprising a determination result that indicates whether the external wireless communication device is in physical contact with the living body;

perform connection processing for establishing a wireless connection to the external wireless communication device, and perform prioritizing processing for prioritizing, in response to an input of the state signal, the connection processing when the external wireless communication device is in physical contact with the living body rather than when the external wireless communication device is not in physical contact with the living body.

* * * * *